(12) United States Patent
Patel et al.

(10) Patent No.: US 6,706,770 B2
(45) Date of Patent: Mar. 16, 2004

(54) CO-PRODUCTION OF HYDROGEN AND METHANOL FROM STEAM REFORMATE

(75) Inventors: Nitin Madhubhai Patel, Allentown, PA (US); Shoou-I Wang, Allentown, PA (US); Eugene S. Genkin, Allentown, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 48 days.

(21) Appl. No.: 10/116,465

(22) Filed: Apr. 4, 2002

(65) Prior Publication Data

US 2003/0191196 A1 Oct. 9, 2003

(51) Int. Cl.$^7$ .............................................. C07C 27/00
(52) U.S. Cl. ..................... 518/705; 518/700; 518/702; 518/704; 518/708; 518/722
(58) Field of Search ................... 518/702, 704, 518/700, 722, 708, 705

(56) References Cited

U.S. PATENT DOCUMENTS

| | | | |
|---|---|---|---|
| 3,940,428 A | 2/1976 | Connell et al. | 260/449.5 |
| 4,181,675 A | 1/1980 | Makin et al. | 260/449.5 |
| 4,271,086 A | 6/1981 | Supp et al. | 518/704 |
| 6,191,174 B1 | 2/2001 | Early et al. | 518/705 |
| 6,214,314 B1 | 4/2001 | Abbott | 423/650 |
| 6,232,352 B1 * | 5/2001 | Vidalin | 518/700 |
| 6,258,860 B1 | 7/2001 | Weedon et al. | 518/706 |

FOREIGN PATENT DOCUMENTS

WO      WO 01/36357        *  5/2001

OTHER PUBLICATIONS

Tindall, B.M. and Crews, M. A., "Alternative Technologies to Steam–Methane Reforming", *Hydrocarbon Processing*, Nov. 1995, pp. 75–82–.
Goff, S.P. and S. I. Wang, "Syngas Production by Reforming", *Chemical Engineering Progress*, Aug. 1987, pp 46–53.

* cited by examiner

Primary Examiner—J. Parsa
(74) Attorney, Agent, or Firm—John M. Fernbacher

(57) ABSTRACT

Method for the production of methanol and hydrogen which comprises steam reforming a hydrocarbon-containing feed in a steam reforming zone to yield a synthesis gas comprising hydrogen, carbon monoxide, and carbon dioxide; introducing a first portion of the synthesis gas into a methanol synthesis zone to form methanol; reacting a second portion of the synthesis gas with steam to convert carbon monoxide to hydrogen and carbon dioxide to yield a shifted synthesis gas; cooling the shifted synthesis gas to yield a cooled shifted synthesis gas; separating the cooled shifted synthesis gas into a high-purity hydrogen product stream and a reject stream enriched in carbon dioxide; and introducing some or all of the reject stream into either or both of the steam reforming zone and the methanol synthesis zone.

13 Claims, 3 Drawing Sheets

CO-PRODUCTION OF HYDROGEN AND METHANOL FROM STEAM REFORMATE

BACKGROUND OF THE INVENTION

A significant portion of the world's methanol is produced by the catalytic reaction of synthesis gas obtained by the steam reforming of light hydrocarbons, particularly natural gas. Steam reforming of light hydrocarbons produces a synthesis gas containing hydrogen, carbon monoxide, and carbon dioxide wherein the synthesis gas composition may be characterized by a hydrogen-carbon oxide molar ratio defined as $$\frac{[H_2] - [CO_2]}{[CO] + [CO_2]}$$

where $[H_2]$, $[CO]$, and $[CO_2]$ are the mole fractions of the respective components in the synthesis gas. Methanol is formed from synthesis gas by the following reactions:

$$CO + 2H_2 \rightarrow CH_3OH$$

$$CO_2 + 3H_2 \rightarrow CH_3OH + H_2O$$

In order to utilize the synthesis gas most efficiently in the above reactions, stoichiometric amounts of hydrogen and carbon oxides are preferred. Synthesis gas with a stoichiometric composition for methanol production has a value of the hydrogen-carbon oxide molar ratio of 2.0. Methanol is produced by reacting the synthesis gas catalytically in a pressurized reactor to yield methanol and unreacted synthesis gas, the methanol is condensed and separated from the unreacted synthesis gas, and a portion of the unreacted synthesis gas is recycled to the reactor feed to increase overall conversion. The remaining unreacted synthesis gas must be purged from the methanol reactor loop so that unreacted components do not build up in the reactor feed gas.

Synthesis gas produced by steam reforming of light hydrocarbons generally contains excess hydrogen when used for methanol production. This means that a significant amount of unreacted hydrogen must be withdrawn in the purge gas, which typically is used as fuel. This purge gas also contains valuable carbon oxides, which become unavailable for conversion to methanol, and this loss adversely affects methanol production economics.

Several approaches to this problem have been utilized in commercial methanol production. In one approach, imported carbon dioxide is mixed with either the synthesis gas feed to the methanol reactor or the feed hydrocarbon to the steam reforming step. This gives a methanol reactor feed gas that is closer to the preferred stoichiometric composition, but is possible only when a source of carbon dioxide is readily available. In another approach, unreacted synthesis gas is separated by various methods into a stream enriched in carbon oxides and a stream enriched in hydrogen, the carbon oxide-rich stream is recycled to the reformer or the methanol reactor, and the hydrogen-enriched stream is used for fuel. Membrane systems, absorption processes, and pressure swing adsorption have been used to effect separation of the unreacted synthesis gas.

An alternative approach is to generate the synthesis gas by methods other than steam reforming wherein these methods produce a synthesis gas closer to the preferred hydrogen-carbon oxide ratio for methanol production. Known methods to generate the preferred synthesis gas composition include the partial oxidation, autothermal reforming, and a two-stage process comprising steam reforming followed by oxygen secondary reforming. These methods all require a supply of oxygen, however, and the capital costs are higher than for simple steam reforming.

Steam reforming of light hydrocarbons continues to be a widely used process for generating synthesis gas for methanol production. It is desirable to develop methods for increasing the net conversion of the hydrocarbon feed to methanol product and for increasing the profitability of methanol production from this synthesis gas. In addition, it is desirable to reduce the cost of co-producing hydrogen and methanol from steam reformate to meet new or existing markets for these two products. The present invention, which is described below and defined by the claims which follow, offers an improved method for the co-production of hydrogen and methanol from synthesis gas generated by the steam reforming of light hydrocarbons.

BRIEF SUMMARY OF THE INVENTION

The invention relates to a method for the production of methanol and hydrogen which comprises steam reforming a hydrocarbon-containing feed in a steam reforming zone to yield a synthesis gas comprising hydrogen, carbon monoxide, and carbon dioxide; introducing a first portion of the synthesis gas into a methanol synthesis zone to form methanol; reacting a second portion of the synthesis gas with steam to convert carbon monoxide to hydrogen and carbon dioxide to yield a shifted synthesis gas; cooling the shifted synthesis gas to yield a cooled shifted synthesis gas; separating the cooled shifted synthesis gas into a high-purity hydrogen product stream and a reject stream enriched in carbon dioxide; and introducing some or all of the reject stream into either or both of the steam reforming zone and the methanol synthesis zone. The hydrocarbon-containing feed may comprise one or more hydrocarbons containing from one to five carbon atoms. The hydrocarbon-containing feed may be natural gas.

The shifted synthesis gas may be separated by pressure swing adsorption. The reject stream from pressure swing adsorption may be introduced into the steam reforming zone or into the methanol synthesis zone.

The method may further comprise withdrawing from the methanol synthesis zone a crude methanol product and unreacted synthesis gas, withdrawing a first portion of the unreacted synthesis gas as purge, and recycling a second portion of the unreacted synthesis gas to the methanol synthesis zone.

The invention also relates to a method for the production of methanol and hydrogen which comprises steam reforming a hydrocarbon-containing feed in a steam reforming zone to form synthesis gas containing hydrogen, carbon monoxide, and carbon dioxide; converting a portion of the synthesis gas to methanol in a methanol synthesis zone; withdrawing from the methanol synthesis zone a crude methanol product and unreacted synthesis gas; recycling a first portion of the unreacted synthesis gas to the methanol synthesis zone; separating a second portion of the unreacted synthesis gas to yield a high-purity hydrogen product stream and a reject stream; recycling a first portion of the reject stream to either or both of the steam reforming zone and the methanol synthesis zone; and utilizing the second portion of the reject stream as fuel to provide heat to the steam reforming zone. The hydrocarbon-containing feed may comprise one or more hydrocarbons containing from one to five carbon atoms. The hydrocarbon-containing feed may be natural gas.

The second portion of the unreacted synthesis gas may be separated by pressure swing adsorption. The first portion of the reject stream may be introduced into the steam reforming zone or the methanol synthesis zone.

DETAILED DESCRIPTION OF THE INVENTION

Figure 1:
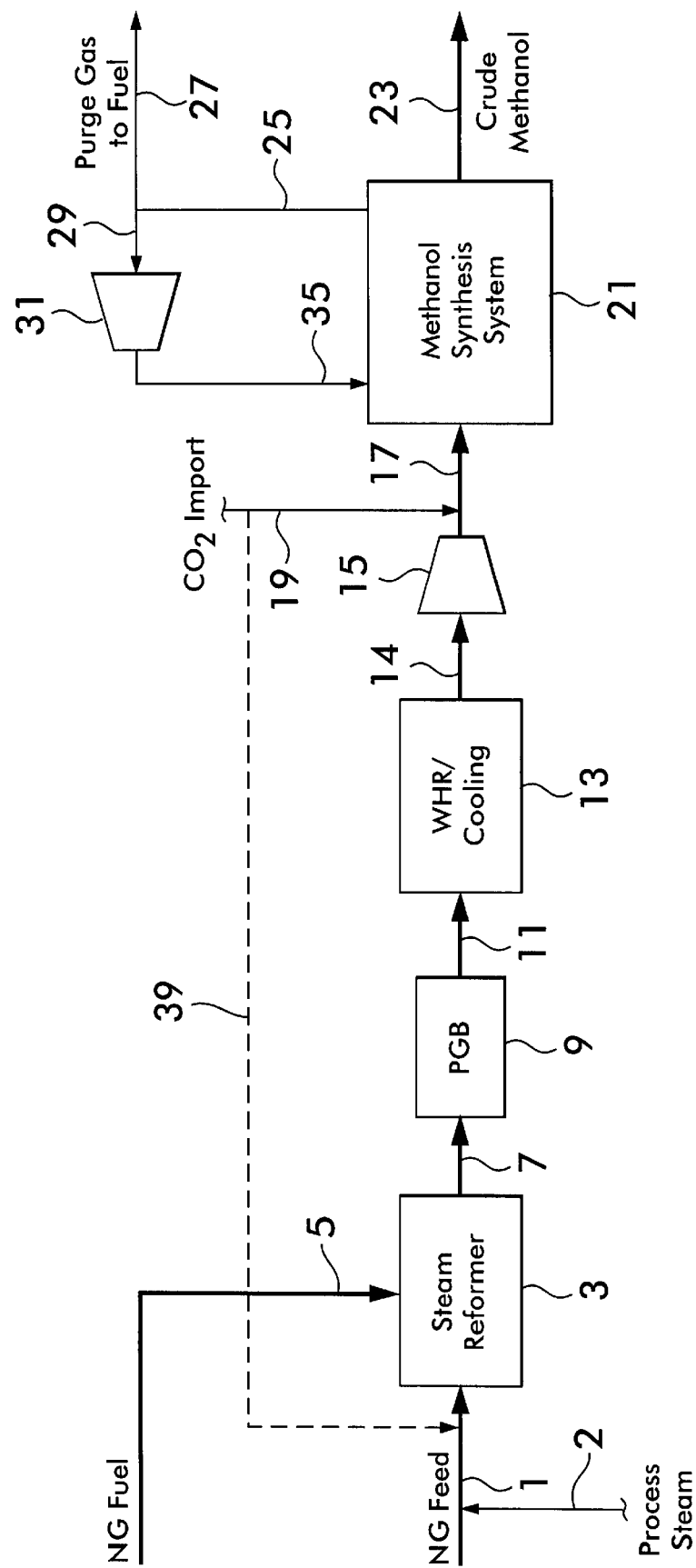
FIG. 1 is a process flow diagram of a prior art process for the production of methanol from synthesis gas generated by steam reforming.

The present invention relates to a method for the co-production of methanol and hydrogen from synthesis gas obtained by steam reforming of light hydrocarbons. The method offers an alternative solution to the inherent problem that steam reforming produces synthesis gas which contains excess hydrogen and is not stoichiometrically balanced for methanol production. The invention may be understood by first reviewing an existing method of producing methanol from steam reformate as illustrated in FIG. 1.

A natural gas (NG) and steam mixture is fed via feed line 1 to steam reformer or steam reforming zone 3 to generate a synthesis gas stream in line 7 containing hydrogen, carbon monoxide, carbon dioxide, unreformed methane, and small amounts of inert gas such as nitrogen. Reformer system 3 includes feed desulfurization if required. Fuel for supplying heat to the endothermic steam reforming reactions is supplied by fuel such as natural gas via line 5. The synthesis gas in line 7 is cooled in process gas boiler (PGB) 9 and the cooled gas in line 11 is further cooled waste heat recovery (WHR) system 13.

Cooled synthesis gas in line 14 is compressed to a pressure of 600 to 1000 psia in compressor 15 and the compressed synthesis gas is combined with imported carbon dioxide via line 19. The imported carbon dioxide typically is compressed to an elevated pressure (not shown) or may be combined with synthesis gas in line 12 prior to compression in compressor 15. The combined gas is fed via line 17 to methanol reactor system or methanol synthesis zone 21. Alternatively, the imported carbon dioxide may be introduced via line 39 into the feed to steam reformer 3 rather than via line 19. In either case, the addition of imported carbon dioxide adjusts the hydrogen-carbon oxide ratio in the methanol reactor system feed towards the preferred value of 2 as discussed above. The imported carbon dioxide may be provided, for example, from a nearby ammonia plant or other process which is supplied by a synthesis gas generation system.

The synthesis gas is partially converted to methanol in methanol synthesis system or zone 21 and the methanol is condensed and separated from the unreacted synthesis gas. Crude liquid methanol product is withdrawn from methanol synthesis system 21 via line 23 for further purification to a final methanol product. Unreacted synthesis gas, which may contain up to 50–55 mole % hydrogen, is withdrawn via line 25 and split into a purge gas stream withdrawn via line 27 and a recycle stream in line 29 which is compressed in compressor 31 and returned via line 35 to methanol synthesis system 21 wherein it is combined with synthesis gas feed from line 17. Purge gas in line 27, which contains unreacted hydrogen and carbon oxides as well as residual inert gas, is typically used as fuel in reformer 3 or elsewhere.

The present invention includes methods to produce hydrogen as a second product while producing methanol from synthesis gas obtained by steam reforming. The invention may be applied to new plant designs in situations where imported carbon dioxide is not available and steam reforming is the preferred method of generating synthesis gas. Alternatively, the invention may be used as a retrofit of an existing methanol plant which utilizes steam reformate as the synthesis gas feed. In these methods, methanol and high purity hydrogen are co-produced to allow maximum utilization of steam reformer capacity and efficiently utilize synthesis gas produced by steam reforming.

Figure 2:
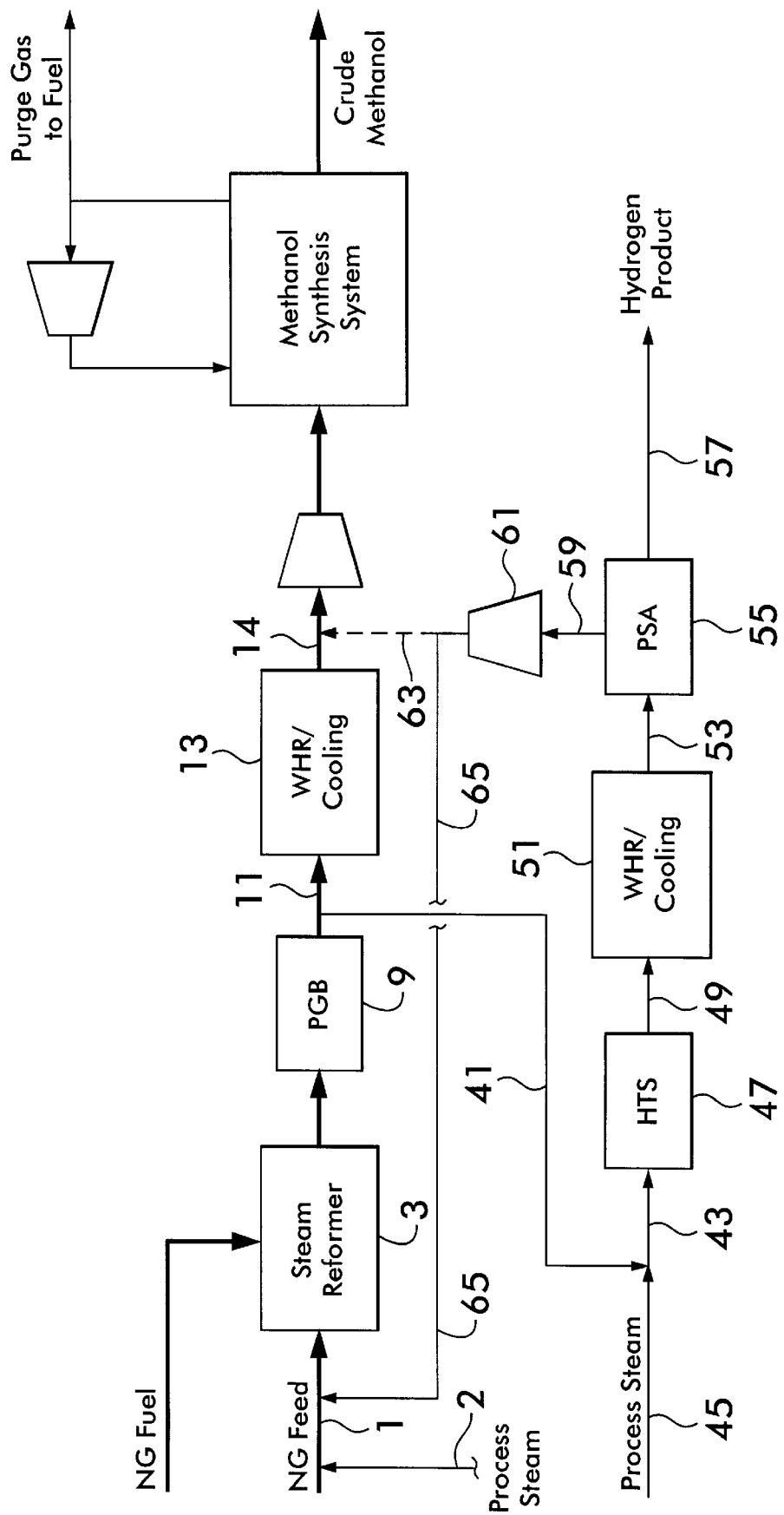
FIG. 2 is a process flow diagram of an exemplary embodiment of the present invention for the co-production of hydrogen and methanol from synthesis gas generated by steam reforming.

One embodiment of the invention is illustrated by way of example in the process flow diagram of FIG. 2. The basic synthesis gas generation and methanol reactor systems may be identical to those described about with reference to FIG. 1. A recycle gas stream (later defined) in line 65 may be combined with the feed gas in line 1 to steam reformer or steam reforming zone 3; alternatively, this recycle gas stream may be combined via line 63 with the cooled synthesis gas in line 14 from waste heat recovery system 13. A portion of the synthesis gas in line 11 from process gas boiler 9 may be withdrawn in line 41, combined with process steam in line 45, and introduced via line 43 into high temperature shift (HTS) system 47. Carbon monoxide and steam are reacted in high temperature shift system 47 to produce additional hydrogen and carbon dioxide, the shifted gas flows via line 49 to waste heat recovery (WHR) cooling system 51, and the cooled, shifted synthesis gas flows via line 53 to pressure swing adsorption (PSA) system 55.

PSA system 55 can utilize any of the well-known multiple-bed adsorption processes for separating hydrogen (a weakly-adsorbed component) from more strongly-adsorbed components including carbon dioxide. High purity hydrogen product typically containing at least 99.9 mole % hydrogen is withdrawn via line 57 and PSA offgas enriched in carbon dioxide is withdrawn via line 59. This carbon dioxide-rich stream is compressed in compressor 61 and recycled via either line 63 or line 65 as described above. It may be desirable in some cases to recycle this carbon dioxide-rich stream via both lines 63 and 65.

Alternatively, instead of utilizing the PSA process described above, hydrogen may be recovered from the shifted synthesis gas by other types of separation processes such as, for example, permeation through a palladium membrane. In this alternative, the hydrogen would be recovered at low pressure compared with the PSA process, which would recover the hydrogen at a higher pressure near the feed pressure.

This embodiment of the invention has two immediate process benefits—a high purity hydrogen product is provided and the hydrogen-carbon oxide ratio of the methanol synthesis system feed is modified to approach the desired stoichiometric value. This reduces purge losses from the methanol synthesis loop and increases the synthesis gas conversion to methanol. This embodiment is especially beneficial when the methanol synthesis system is operating below the design rate, because hydrogen can be produced to keep the reformer and other upstream equipment operating close to the design rate. This embodiment also provides good flexibility in the co-production of hydrogen and methanol to meet variable product requirements.

Figure 3:
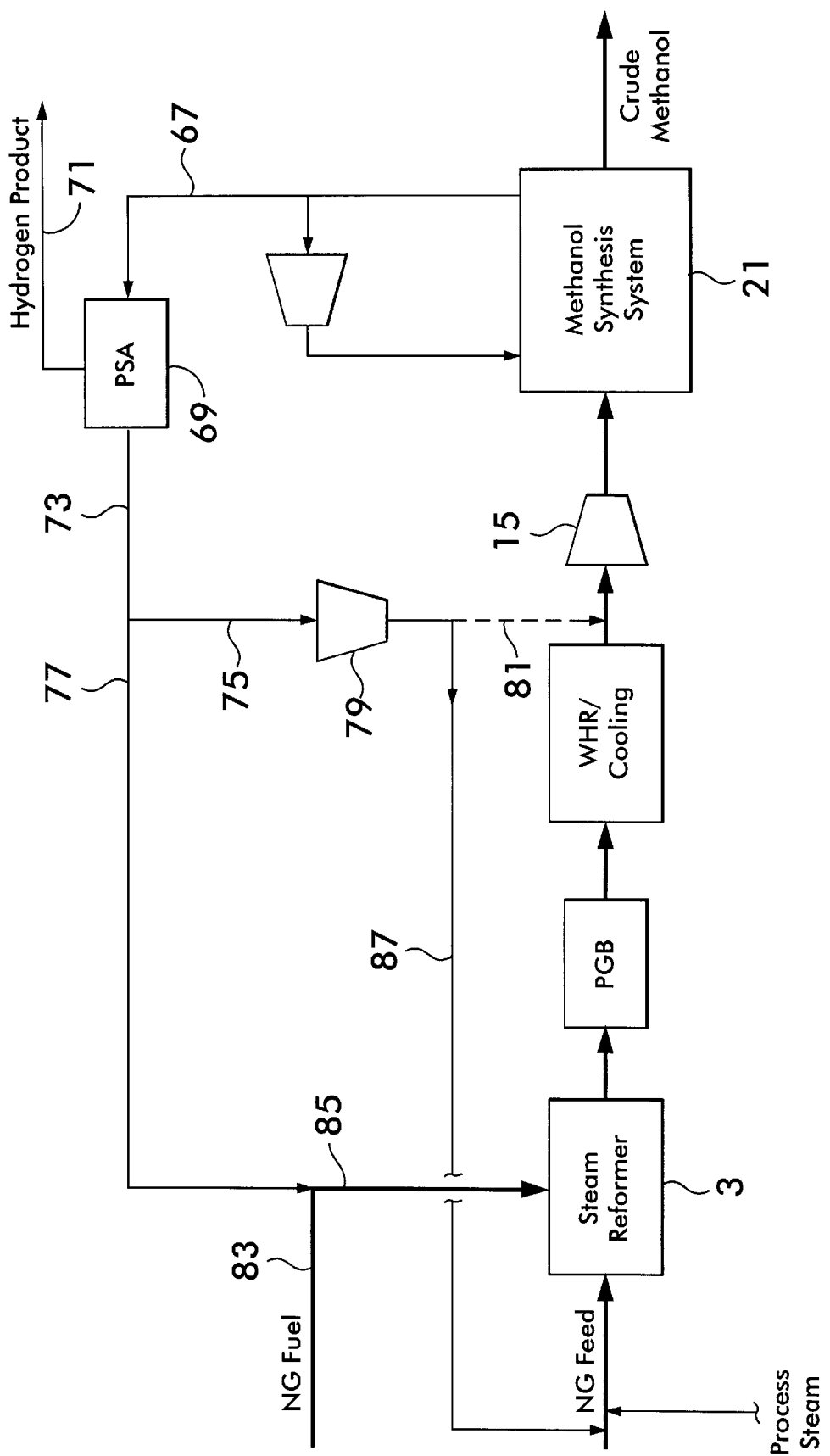
FIG. 3 is a process flow diagram of another exemplary embodiment of the present invention for the co-production of hydrogen and methanol from synthesis gas generated by steam reforming.

An alternative exemplary embodiment of the invention is illustrated by the process flow diagram of FIG. 3. In this embodiment, the basic synthesis gas generation and methanol synthesis systems may be identical to those described above with reference to FIGS. 1 and 2. Methanol synthesis system purge gas, which may contain up to 50–55 mole % hydrogen, is withdrawn via line 67 and separated in PSA system 69 to yield a high purity hydrogen product stream via line 71 and offgas enriched in carbon monoxide and carbon dioxide via line 73. A portion of this offgas stream via line 77 is combined with natural gas or other fuel in line 83 to provide fuel via line 85 for steam reformer 3. Using a portion of the PSA offgas for reformer fuel provides for purge from the methanol reactor loop. The remaining portion of the PSA offgas in line 73 is withdrawn via line 75, compressed in compressor 79, and recycled via line 87 to the feed inlet of steam reformer 3. Alternatively, the PSA offgas may be recycled via line 81 to the inlet of compressor 15 to provide the carbon oxides directly to methanol synthesis system 21. It may be desirable in some cases to recycle this carbon oxide-rich stream via both lines 81 and 87.

In this embodiment of the invention, as in the previous embodiment, two immediate process benefits are realized—high purity hydrogen is produced and the hydrogen-carbon oxide ratio of the methanol synthesis system feed is modified to approach the desired stoichiometric value.

The embodiments described above with reference to FIGS. 2 and 3 have general economic and operating benefits compared with the conventional process of FIG. 1 or other known processes. The co-production of hydrogen and methanol yields improved energy efficiency and lower capital costs compared with a standalone reforming process to make hydrogen. For example, the energy efficiency of the process embodiment of FIG. 2 may be 355 to 360 BTU/ standard cubic foot of hydrogen compared with 380 to 400 BTU/standard cubic foot of hydrogen from a conventional standalone reforming process. By recycling carbon oxides back to the methanol synthesis loop, the reactor feed gas can be maintained close to the preferred stoichiometric ratio for methanol synthesis. Carbon dioxide import can be reduced significantly or eliminated completely. The methanol conversion per pass in the methanol reactor loop can be increased due to lower hydrogen buildup in the loop, and as a result the purge rate can be reduced to minimize carbon oxide losses.

When no carbon dioxide is available for import and light hydrocarbon feedstock is used for synthesis gas generation, the present invention can be used as a low-cost alternative to oxygen secondary reforming, particularly when a hydrogen co-product is desired. The embodiments of the invention also provide improved operational and commercial flexibility for the co-production of methanol and hydrogen, and improve asset utilization of the steam reformer and related front-end process equipment.

What is claimed is:

1. A method for the production of methanol and hydrogen which comprises steam reforming a hydrocarbon-containing feed in a steam reforming zone to yield a synthesis gas comprising hydrogen, carbon monoxide, and carbon dioxide; introducing a first portion of the synthesis gas into a methanol synthesis zone to form methanol; reacting a second portion of the synthesis gas with steam to convert carbon monoxide to hydrogen and carbon dioxide to yield a shifted synthesis gas; cooling the shifted synthesis gas to yield a cooled shifted synthesis gas; separating the cooled shifted synthesis gas into a high-purity hydrogen product stream and a reject stream enriched in carbon dioxide; and introducing some or all of the reject stream into either or both of the steam reforming zone and the methanol synthesis zone.

2. The method of claim 1 wherein the hydrocarbon-containing feed comprises one or more hydrocarbons containing from one to five carbon atoms.

3. The method of claim 2 wherein the hydrocarbon-containing feed is natural gas.

4. The method of claim 1 wherein the shifted synthesis gas is separated by pressure swing adsorption.

5. The method of claim 1 wherein the reject stream is introduced into the steam reforming zone.

6. The method of claim 1 wherein the reject stream is introduced into the methanol synthesis zone.

7. The method of claim 1 which further comprises withdrawing from the methanol synthesis zone a crude methanol product and unreacted synthesis gas, withdrawing a first portion of the unreacted synthesis gas as purge, and recycling a second portion of the unreacted synthesis gas to the methanol synthesis zone.

8. A method for the production of methanol and hydrogen which comprises steam reforming a hydrocarbon-containing feed in a steam reforming zone to form synthesis gas containing hydrogen, carbon monoxide, and carbon dioxide; converting a portion of the synthesis gas to methanol in a methanol synthesis zone; withdrawing from the methanol synthesis zone a crude methanol product and unreacted synthesis gas; recycling a first portion of the unreacted synthesis gas to the methanol synthesis zone; separating a second portion of the unreacted synthesis gas to yield a high-purity hydrogen product stream and a reject stream; recycling a first portion of the reject stream to either or both of the steam reforming zone and the methanol synthesis zone; and utilizing the second portion of the reject stream as fuel to provide heat to the steam reforming zone.

9. The method of claim 8 wherein the hydrocarbon-containing feed comprises one or more hydrocarbons containing from one to five carbon atoms.

10. The method of claim 9 wherein the hydrocarbon-containing feed is natural gas.

11. The method of claim 8 wherein the second portion of the unreacted synthesis gas is separated by pressure swing adsorption.

12. The method of claim 8 wherein the first portion of the reject stream is introduced into the steam reforming zone.

13. The method of claim 1 wherein the first portion of the reject stream is introduced into the methanol synthesis zone.

* * * * *